United States Patent [19]

Sumino et al.

[11] Patent Number: 4,791,061

[45] Date of Patent: Dec. 13, 1988

[54] IMMOBILIZATION OF MICROORGANISMS BY ENTRAPMENT

[75] Inventors: Tatsuo Sumino; Yasutomo Ohtake; Hiroki Nakamura; Masahiro Kon; Naomichi Mori; Kazuo Nakajima, all of Chiyoda, Japan

[73] Assignee: Hitachi Plant Engineering & Construction Co., Ltd., Tokyo, Japan

[21] Appl. No.: 868,454

[22] Filed: May 30, 1986

[30] Foreign Application Priority Data

Jun. 28, 1985 [JP] Japan .................................. 60-141901
Sep. 13, 1985 [JP] Japan .................................. 60-202877

[51] Int. Cl.$^4$ ..................... C12N 11/10; C12N 11/04; C12N 11/02
[52] U.S. Cl. ................................. 435/178; 435/176; 435/177; 435/182; 435/261; 435/262
[58] Field of Search .............. 435/174, 177, 178, 182, 435/176, 261, 262

[56] References Cited

U.S. PATENT DOCUMENTS

| | | | |
|---|---|---|---|
| 4,452,892 | 6/1984 | Rosevear | 435/182 X |
| 4,578,351 | 3/1986 | Rosevear et al. | 435/182 X |
| 4,605,622 | 8/1986 | Hasegawa et al. | 435/182 |
| 4,634,672 | 1/1987 | Baumgarten et al. | 435/182 |

Primary Examiner—David M. Naff
Attorney, Agent, or Firm—Sughrue, Mion, Zinn, Macpeak, and Seas

[57] ABSTRACT

Microorganisms such as in activated sludge are immobilized by forming a mixture containing the microorganisms, a monomer or prepolymer and alginic acid or water soluble alignate, and dropping the mixture into a water solution of polyvalent metal ion and a polymerization initiator to form particles containing the microorganisms. Preferably, the monomer is an acrylamide monomer, the prepolymer is an ester of an acrylic acid group and polyethylene glycol and the polymerization initiator is a persultate. By this method, the microorganisms are protected from toxic substances such as the polymerization initiator during immobilization.

11 Claims, 3 Drawing Sheets

IMMOBILIZATION OF MICROORGANISMS BY ENTRAPMENT

BACKGROUND OF THE INVENTION

1. Field of the Invention

This invention relates to a method of immobilizing microorganisms entrapped in pellets of polyurethane, polyethylene glycol or polyacrylamide as in the activated state.

2. Description of the Prior Art

Methods of biological waste treatment include an activated sludge method. According to the activated sludge method, the microorganisms (sludge) is suspended in the waste water and the treatment is carried out as the suspended microorganisms prolixerate, and, normally, under the conditions of the BOD volume load 0.6~0.8 Kg-BOD/$m^3$ per day, about 50% of the removed BOD is converted into sludge. The sludge conversion rate is calculated by a formula of the sludge production (Kg)/the removed BOD (Kg). Furthermore, according to a method of biomembrane, there are living very small animals and Protozoa. Since the very small animals and Protozoa take in the produced microorganisms as feeds, the sludge conversion rate is about 30%.

The sludge conversion rate is so high as 50% according to the activated sludge method and as 30% according to the biomembrane immobilizing method. In consequence, the surplus sludge thus produced is removed from a settling basin, dehydrated and disposed by burning, reclaiming and the like, whereby the disposal of surplus sludge needs an enormous cost.

Then, recently, there has been proposed biological waste treatment methods of immobilizing the microorganisms in the activated sludge into a polymeric carrier or an inorganic carrier. These methods include a method, wherein the microorganisms or activated sludge used in the waste water treatment is immobilized into a polymeric carrier having a large surface area and an entrappingly immobilizing method of entrapping microorganisms and the like when high polymer molecules are formed from monomer. The above-described polymeric immobilizing carrier can carry out the biological waste treatment of waste water when in contact with the waste water. According to this carrier immobilizing method, the sludge conversion rate is 10% or less, so that production of surplus sludge is low.

Now, as a carrier for immobilizing the microorganisms, there has been proposed a synthetic polymer such as polyethylene and the like. When resin, porous glass or natural substance is used as the carrier, anyone of these materials is low in toxicological properties to the microorganisms, so that reduction in activity of the immobilized microorganisms is low. However, the immobilized substance is low in physical strength and presents a disadvantage in durability.

Furthermore, as the entrappingly immobilizing method, there is conceived one, wherein monomer or prepolymer (low molecular weight polymer being soluble) having a terminal bond group or groups and having a molecular weight of approx 300 to 5000 are polymerized, and entrapped in a polymeric carrier such as polyacrylamide, epoxy resin, polystyrene, polyvinyl alcohol and the like.

However, when the microorganisms are entrappingly immobilized in polyurethane for example, the immobilized microorganisms thus obtained are very high in physical strength and satisfactory in durability. However, a solution of polyurethane prepolymer used at the time of immobilizing renders a toxic effect to the microorganisms, whereby reduction in activity of the microorganisms tends to be caused.

Similarly, when the microorganisms are immobilized into polyacrylamide resin, acrylamide monomer, a crosslinker, a polymerization initiator and the like render a toxic effect to the microorganisms, so that most of the microorganisms become extinct. Particularly, most of the weak bacteria such as nitrification bacteria become extinct, and, it takes much time to proliferate the remaining bacteria.

SUMMARY OF THE INVENTION

The present invention has been developed to obviate the above-described disadvantages of the prior art and has as its object the protection of microorganisms from toxicological properties of monomer or prepolymer when the monomer or prepolymer is used. Another object of the present invention is to polymerize the monomer or prepolymer and entrappingly immobilize the microorganisms into the polymer.

The present invention contemplates that microorganism-suspended liquid, alginic acid or water-soluble alginate, and monomer or prepolymer rendering a toxic effect to the microorganisms are mixed to provide a solution. This mixed solution is dropped into a salt solution forming an insoluble salt with alginic acid, and particles of insoluble salt of alginic acid, which entrap the microorganisms, are formed, whereby the microorganisms are held within these particles and the monomer or polymer is polymerized to entrappingly immobilize the microorganisms, so that reduction in activity of the microorganisms, which would otherwise have occurred, can be avoided.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Figure 1:
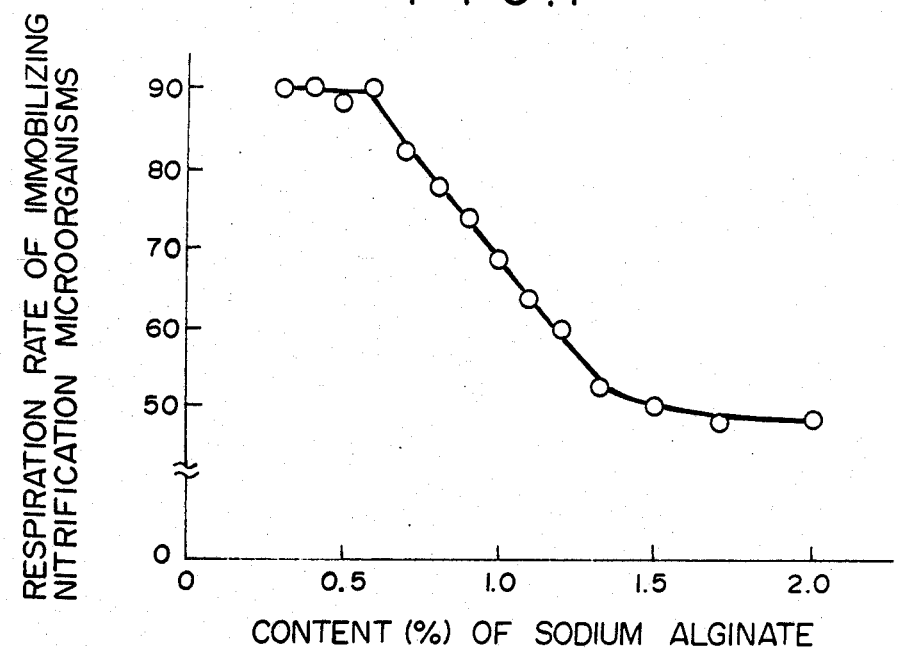
FIG. 1 is a graphic chart showing the relationship between the amount of sodium alginate and the respiration rate of the immobilized nitrification bacteria.

Detailed description will hereunder be given of the preferred embodiment of an apparatus for working the method of immobilizing the microorganisms according to the present invention with reference to the accompanying drawings.

The mixed solution according to the present invention is added thereto with microorganisms living in the activated sludge, and the microorganisms are entrapped in a high polymeric substance formed of monomer or prepolymer (low molecular weight polymeric substance). As the microorganisms in the activated sludge, there are living the nitrification bacteria (nitrifying bacteria, nitrobacter) methane bacteria, Pseudomonous sp., Flavobacterium sp. and so on. These microorganisms are entrapped in polymer.

Alginic acid to be added to the mixed solution according to the present invention is added to the mixed solution as soluble alginate, which is sodium alginate, potassium alginate or ammonium alginate.

As prepolymer added to the mixed solution, these are used polyurethane polymer having an averge molecular weight of 1000 to 4000, polyethylene glycol, wherein a polymeric active group or groups of acrylic acid, methacrylic acid or the like are esterified, having a molecular weight of 300 to 2000, and the like. Furthermore, as monomer, acrylamide monomer is used.

Furthermore, as the salt, which forms insoluble salt with alginic salts, there are used calcium salt, barium salt, aluminum salt, methylene blue, ferric ions or the like. Mainly, cation salt having the valence of 2 or more is taken into a water solution for use.

Detailed description will hereunder be given of the method of immobilizing the microorganisms according to the present invention by use of a solution of polyurethane prepolymer. Polyurethane prepolymer used in the present invention can be manufactured according to the well-known method in such a manner that di-isocyanate, tri-isocyanate or other poly-isocyanate is caused to react to a compound containing active hydrogen, particularly, glycol, polyglycol, polyester polyol, or polyether polyol.

Polyurethane prepolymer used in the present invention has an average molecular weight of 1000 to 4000 and contains isocyanate groups of 1.0 to 4%.

It is conceivable that lowered activity of the microorganisms in the case of immobilizing the microorganisms by use of polyurethane prepolymer is caused due to the toxicological properties of chemicals such as isocyanate groups in polyurethane prepolymer in the solution of polyurethane prepolymer, residual monomer, the crosslinker and plasticizer.

According to the present invention, a mixed solution including polyurethane prepolymer, alginic acid or a water-soluble salt of alginic acid (here in after, description will be given of sodium salt as an example), and microorganisms is dropped into a water solution of a salt forming an insoluble salt with alginic acid (description will be given of calcium chloride as an example), whereby particles of calcium alginate entrapping the microorganisms are formed, and simultaneously, polyurethane prepolymer held within the particles is polymerized. According to this method, when the mixed solution is dropped into a water solution of calcium chloride, a substance having a low molecular weight leaks through perforations of calcium alginate and is diffused in the water solution of calcium chloride. Particularly, residual monomer, crosslinker, plasticizer and the like, which have low molecular weight, are instantaneously diffused, and polyurethane prepolymer having a low molecular weight tends to be diffused in the water solution of calcium chloride. Polyurethane prepolymer having a high molecular weight leaks not easily, and is polymerized within the particles of calcium alginate. In consequence, the microorganisms, being in contact with the chemicals such as the crosslinker and plasticizer for a short period of time so as not to be subjected to the toxicological properties, can hold the activity thereof to a high extent. If a crosslinker such as toluene diisocyanate is mixed with the mixed solution immediately before the dropping, then the microorganisms, being in contact with the chemical for further shorter period of time, increase the activity thereof.

By varying the concentration of sodium alginate, nitrifying bacteria are immobilized according to the present invention, and the activity of nitrification bacteria is measured from the oxygen absorption of nitrification bacteria. The results are shown in FIG. 1. As apparent from FIG. 1, it is preferable to add 0.3~1.2% of sodium alginate, and more preferably, 0.3~0.6% thereof. It is conceivable that, when the concentration of sodium alginate is high, the toxic substance not easily leaks into the solution of calcium chloride.

Figure 2:
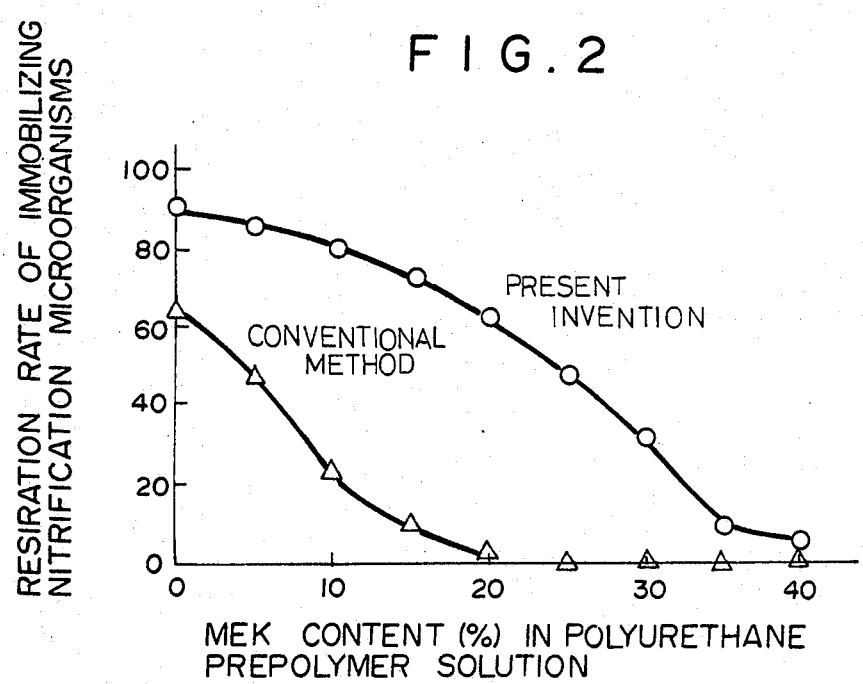
FIG. 2 is a graphic chart showing the relationship between the amount of methyl ethyl ketone in polyurethane prepolymer and the respiration rate of the immobilized nitrification bacteria.

By using methyl ethyl ketone as the plasticizer and varying the concentration of methyl ethyl ketone in the solution of polyurethane prepolymer, nitrification bacteria are immobilized according to the present invention, and the rate of residual activity of nitrification bacteria is measured from the oxygen absorption thereof. The results are shown in FIG. 2. In this case, 12% of the solution of polyurethane prepolymer and 0.5% of sodium alginate are used. As is apparent from FIG. 2, it is preferable that the addition of methyl ethyl ketone is 30% or less. Since the solution of polyurethane prepolymer is high in viscosity, it is preferable to add methyl ethyl ketone, and the addition of 5~30% is preferable.

Figure 3:
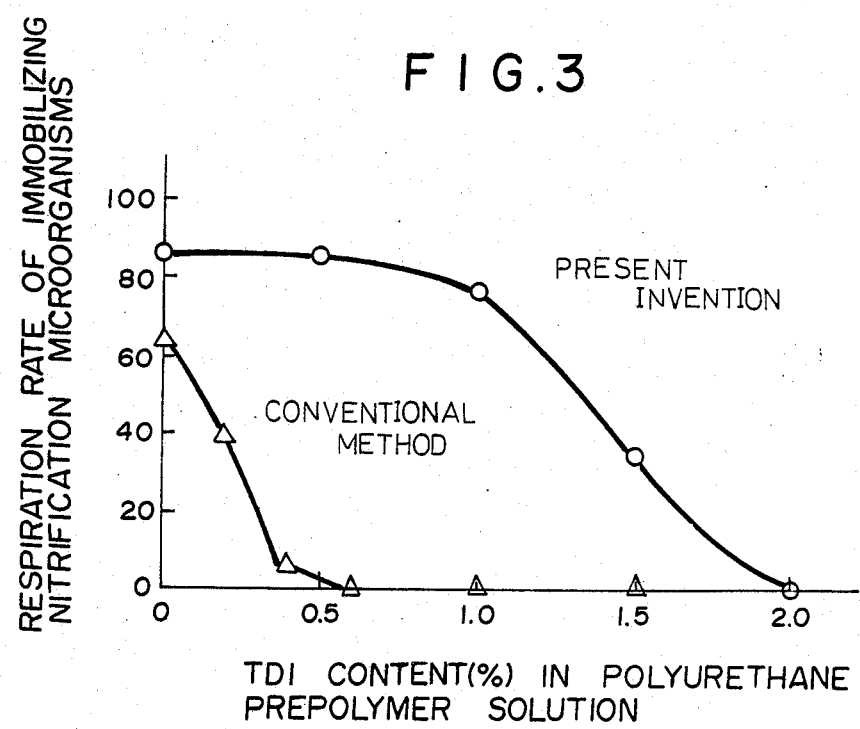
FIG. 3 is a graphic chart showing the relationship between the amount of toluene diisocyanate in polyurethane prepolymer and the respiration rate of the immobilized nitrification bacteria.

Further, according to the present invention, by using toluene diisocyanate as a denaturing agent and varying the concentration of toluene diisocyanate in the solution of polyurethane prepolymer, nitrification bacteria are immobilized, and the rate of residual activity of nitrification bacteria is measured from the oxygen absorption thereof. The results are shown in FIG. 3. In this case also, the solution of polyurethane prepolymer of 12% and sodium alginate of 0.5% are used. As apparent from FIG. 3, it is preferable to add toluene diisocyanate of 1.5% or less, and more preferably, 0.8% or less.

Additionally, if a small amount of toluene diisocyanate is not contained in the solution of toluene diisocyanate, then the solution itself reacts to moisture in the air and is polymerized. In consequence, it is preferable to contain toluene diisocyanate of 0.2~0.8%. Furthermore, methyl ethyl ketone is used for cleaning, etc., of pipings and a reaction tank in a production line of the solution of polyurethane prepolymer, indispensable to the industrial production, and a small amount thereof is to be contained in the solution of polyurethane prepolymer.

Examples, wherein polyurethane polymer is used, will hereunder be shown.

EXAMPLE 1

As the spores, there was used the activated sludge obtained in the waste water treatment center K in Matsudocity, and tests were conducted on nitrification bacteria obtained by acclimatizing this activated sludge by composite waste water containing glucose, methane bacteria under anaerobic conditions by waste water containing glucose, and Pseudomonous sp. and Flavobacterium sp. which were separated from the activated sludge.

Production of immobilized microorganisms according to the present invention

The activated sludge was thickened to 4000 mg/l, 5 ml of sodium alginate of 2% was added to 10 ml of this thickened solution, the solution thus obtained was added thereto with 0.75~2.4 g of polyurethane prepolymer containing 0~16% of methyl ethyl ketone (hereinafter referred to briefly as "MEK") and 0~1.2% of toluene isocyanate (hereinafter referred to briefly as "TDI"), agitated well, and dropped into a solution of calcium chloride of 2.5%, whereby immobilized microorganisms in spherical shapes each having a diameter of 2~3 mm were obtained.

Production of immobilized microorganisms according to the conventional method

Water of 5 ml was added to the thickened solution of 10 ml, the solution thus obtained was added thereto with 0.75 g~2.4% of polyurethane prepolymer containing 0~16% of MEK and 0~1.2% of TDI, agitated well, caused to flow on a polyethylene film, immobilized into a film shape having a thickness of 2 mm, and formed into a cube having a volume of 2 mm.

Similarly, nitrification bacteria, methane bacteria, Pseudomonous sp. and Flavobacterium sp. were immobilized according to the present invention and the conventional method.

Measuring of the activities

Each of the immobilized microorganisms was measured in its activity. The activity was measured such that, for the activated sludge and nitrification bacteria, the respiration rates (unit: $mgO_2/h$) were measured, and, for methane bacteria, Pseudomonous sp. and Flavobacterium sp., the numbers of live bacteria were measured. The results are shown in a table shown below. The respiration rate was measured such that the total amount of the immobilized microorganisms thus produced was put into an incubator bottle of 110 ml, and the respiration rate was measured from the decrease of dissolved oxygen.

As apparent from the table, the present invention was advantageous in that high values in the respiration rate and the number of live bacteria were obtained as compared with the conventional method.

FIGS. 2 and 3 show the result of that, according to the conventional method, nitrification bacteria were immobilized into a film shape in a concentration of bacteria similarly to the above, and influences rendered by MEK and TDI were measured. From this result, it is found that the method according to the present invention is more advantageous than the conventional method. According to the present invention, the microorganisms can be entrappingly immobilized in the highly activated state by polyurethane. Furthermore, when nitrification bacteria are acclimated as will be described hereunder, in the above-described example 1, about 100 mg/l (above the solubility) of calcium phosphate may be added for cultivation, and the concentration of nitrification bacteria is increased as high as three times the concentration of nitrification bacteria in the conventional method, i.e. to MLSS 30000 mg/l.

| BACTERIA | ADDITION OF POLYURETHAN PREPOLYMER (%) | MEK CONVENTION IN POLYURETHAN PREPOLYMER (%) | TDI CONVENT IN POLYURETHAN PREPOLYMER (%) | ADDITION OF BACTERIA (%) | ADDITION OF SODIUM ALGINATE (%) | ACTIVITY OF IMMOBILIZED BACTERIA | |
|---|---|---|---|---|---|---|---|
| | | | | | | THIS INVENTION | CONVENTIONAL METHOD |
| ACTIVATED SLUDGE | 12 | 12 | 0.6 | 2 | 0.5 | 94 | 4 |
| | 12 | 0 | 0 | 2 | 0.5 | 135 | 63 |
| | 12 | 12 | 0 | 2 | 0.5 | 110 | 45 |
| | 12 | 0 | 1.2 | 2 | 0.5 | 102 | 0 |
| NITORIFICATION BACTERIA | 12 | 12 | 0.6 | 1 | 0.5 | 38 | 0 |
| | 12 | 14 | 0.6 | 1 | 0.5 | 36 | 0 |
| | 14 | 14 | 1.0 | 2 | 0.5 | 70 | 0 |
| | 15 | 14 | 0 | 2 | 0.4 | 80 | 22 |
| | 16 | 0 | 0 | 2 | 0.5 | 92 | 63 |
| METHANE BACTERIA | 10 | 10 | 0.6 | 2.5 | 0.4 | $1.2 \times 10^9$ | $2.3 \times 10^2$ |
| | 12 | 12 | 0 | 2.5 | 0.4 | $3.1 \times 10^{10}$ | $8.4 \times 10^8$ |
| | 14 | 14 | 0 | 2.5 | 0.4 | $1.2 \times 10^{10}$ | $3.5 \times 10^8$ |
| PSEUDOMONOUS SP. | 8 | 8 | 0.6 | 0.5 | 0.3 | $4.5 \times 10^9$ | $2.3 \times 10^2$ |
| | 12 | 0 | 0 | 0.5 | 0.3 | $7.3 \times 10^{10}$ | $3.7 \times 10^8$ |
| | 16 | 16 | 0 | 0.5 | 0.3 | $1.5 \times 10^{10}$ | $1.4 \times 10^7$ |
| FLAVOBACTERIUM SP. | 5 | 5 | 0.4 | 0.5 | 0.3 | $3.6 \times 10^9$ | $1.0 \times 10^2$ |
| | 10 | 0 | 0 | 0.5 | 0.3 | $7.2 \times 10^{10}$ | $4.3 \times 10^8$ |
| | 15 | 15 | 0 | 0.5 | 0.3 | $1.3 \times 10^{10}$ | $5.3 \times 10^7$ |

Figure 4:
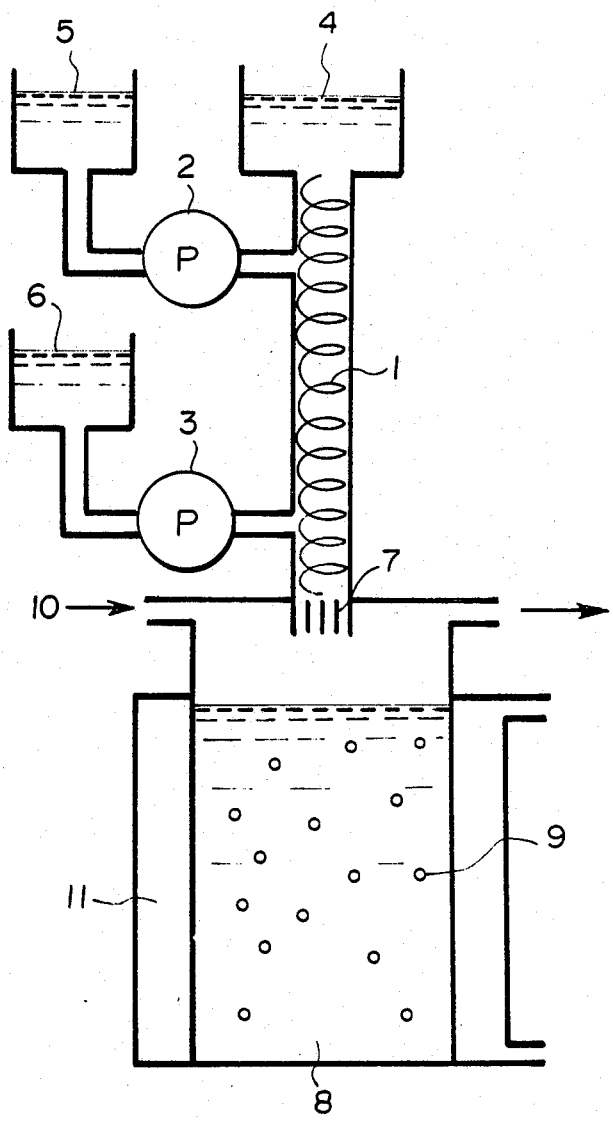
FIG. 4 is a schematic flow chart showing a specific form of the apparatus working the method according to the present invention.

Description will hereunder be given of a method, wherein acrylamide monomer is used in the method of immobilizing the microorganisms according to the present invention with reference to FIG. 4 shows the specific form of an apparatus for working the method according to the present invention. In the apparatus shown in the drawing, firstly, a microorganisms-suspension (activated sludge) 4, water solution of sodium alginate 5 and water solution of acrylamide monomer 6 are mixed with one another by use of a line mixer 1 and pumps 2 and 3. Further, when the mixed solution thus obtained is dropped through a nozzle 7 connected to the line mixer 1 into a water solution 8 of polymerization initiator and calcium chloride, particles of calcium alginate are formed, and simnltaneously, polymerization of acrylamide monomer is initiated within the particles, and particle shaped immobilized microorganisms 9 are completed information in about 3~15 min. The particle diameter is variable in accordance with the viscosity of the dropping mixed solution and the adjusting of the bore diameter of the nozzle 7, and the particle diameter of 1~8 mm is obtainable. Gas 10 not containing oxygen such as nitrogen can be passed through the nozzle 7 portion so as to form the anaerobic atmosphere. It is necessary for the water solution 8 of the polymerization initiator to prevent temperature rise due to the heat at the time of polymerization, and the water solution 8 is held at 20°~35° C. by use of a water jacket 11.

The concentration of the mixture of sodium alginate and acrylamide monomer, which are mixed with each other in the line mixer 1 can be suitably varied, and normally, the mixture is made such that, in the mixed solution, the concentration of sodium alginate is 0.1~2% and the concentration of acrylamide monomer is 5~30%.

Additionally, according to the present invention, the gas not containing oxygen such as nitrogen is previously and satisfactorily passed through the water solution containing calcium chloride and the polymerization initiator, whereby dissolved oxygen hampering the polymerization is eliminated and the operation is carried out under the anaerobic atmosphere, so that acrylamide monomer held within the dropped particles can be reliably polymerized in a short period of time.

According the method of the present invention, normally as the crosslinkers, N,N'-methylene-bis-acrylamide, N,N'-propylene-bis-acrylamide, diacrilamidedimethylester, and the like are dissolved in the solution of monomer, and further, as necessary, as the polymerization promoter, β-dimethybaminopropylnitrile, N,N,N',N'-tetramethylethylenediamine or the like for example is dissolved.

An example, wherein acrylamide monomer is used, and a conventional comparative example will hereunder be shown.

EXAMPLE 2

Firstly, Solutions A~D having each of the following compositions were prepared.
Solution A: Pseudomonous sp. $6.5 \times 10^7$ cells/cm$^3$ suspension
Solution B: water solution of 15% of sodium alginate
Solution C: mixed water solution of 54% of acrylamide monomer, 3% of N,N'-methylene-bis-acrilamide and 1.5% of β-dimethylaminopropylnitrile
Solution D: Mixed water solution of 1% of calcium chloride and 0.5% of peroxo potassium disulfate Solutions A, B and C were equivalently mixed by use of the apparatus shown in the drawing, and dropped into Solution D, which was previously and satisfactorily passed therethrough with nitrogen gas. The bore diameter of the nozzle was 1.5 mm. Calcium alginate was produced and the polymerization of acrylamide was initiated. Temperature of Solution D was held at 30° C., and Solution D was slowly agitated to prevent the particles from adhering to one another. Polymerization was completed in several minutes and the immobilized microorganisms were obtained.

The particle diameter of the immobilized microorganisms was 3~4 mm and the respiratory activity was 35% of the free microorganisms.

EXAMPLE 3

Firstly, Solutions A~D having each of the following compositions were prepared.
Solution A: Flavobacterium sp. $2.3 \times 10^7$ cells/cm$^3$ suspension
Solution B: water solution of 3% of sodium alginate
Solutions C and D: same as in EXAMPLE b 2

The immobilized microorganisms were produced according to a method similar to the one in EXAMPLE 2. The particle diameter was 4~5 mm, and the respiratory activity was 78% of the free microorganisms.

Comparative Example 1

Solutions A~C having each of the following compositions were prepared.
Solution A: Pseudomonous sp. $4.3 \times 10^8$ cells/cm$^3$ suspension
Solution B: water solution of 36% of acrylamide monomer, 2% of N,N'-methylene-bis-acrylamide and 1% of β-dimethylaminopropylnitrile
Solution C: toluene (73% V/V)+chloroform (27% V/V)

Solutions B and C were equivalently mixed with each other, dropped into Solution C, which was slowly agitated, by use of a nozzle having a bore diameter of 1.5 mm. Temperature of Solution C was held at 30° C. Polymerization was completed in several minutes and particles of immobilized microorganisms each having a particle diameter of 3~4 mm were obtained. The respiratory activity was b 5% of the free microorganisms.

Comparative Example 2

Solutions A~C having each of the following compositions were prepared.
Solution A: Flavobacterium sp. $1.5 \times 10^7$ cells/cm$^3$ suspension
Solutions B and C: Same as in COMPARATIVE EXAMPLE 1

The immobilized microorganisms were produced according to a method similar to the one in COMPARATIVE EXAMPLE 1. The particle diameter was 4~5 mm and the respiratory activity was 11% of the free microorganisms.

According to the present invention, particle-shaped immobilized microorganisms can be obtained without using hydrophobic solution, and the immobilized microorganisms hold remarkably high activity as compared with ones produced according to the conventional method.

Detailed description will hereunder be given of the method of immobilizing the microorganisms according to the present invention, wherein a polymerization active group or groups are bonded to polyethylene glycol to form prepolymer of polyethylene glycol, this prepolymer is formed into polymeric gel and the microorganisms are entrappingly immobilized in the polymeric gel.

Polyethylene glycol used as the prepolymer in the present invention is ester-linked thereto with acrylic acid or methacrylic acid. One or more of acrylic acid or methacrylic acid can be bonded to polyethylene glycol through esterification. The molecular weight of polyethylene glycol bonded thereto with acrylic acid or methacrylic acid, which is esterified, is preferably about 300~5000.

To describe in detail, as monoester of methoxypolyethylene glycol, there may be listed
(1) methoxytetraethylene glycol methacrylate, (2) methoxypolyethylene glycol #400 methacrylate, and (3) methoxypolyethylene glycol #1000 methacrylate. As polyethylene glycol diester, it is preferable to use (4) polyethylene glycol #200 dimethacrylate, (5) polyethylene glycol #400 dimethacrylate, (6) polyethylene glycol #1000 dimethacrylate, (7) 2,2-bis[4-(methacryloxy-polyethoxy)phenyl]-propane, (8) polyethylene glycol #200 diacrylate, (9) polyethylene glycol #400 diacrylate, and (10) polyethylene glycol #600 diacrylate, for example.

An example wherein polyethylene glycol acrylate is used, will hereunder be shown.

EXAMPLE 4

The activated sludge was thickened to 40000 mg/l, 18% of polyethylene glycol diacrylate and 0.5% of sodium alginate was added to thickened solution, the solution thus obtained was well agitated, dropped into solution of calcium chloride of 2.5% containing β-dimethylaminopropionitrile (polymerization promotor) and potassium persulfate by use of a syringe, and spherical particles of immobilized microorganisms each having a diameter of 2~3 mm were obtained. Production of the immobilized microorganisms according to the conventional method.

The above-described thickened liquid is added thereto with 18% of polyethylene glycol acrylate, 0.5% of β-dimethylaminopropionitrile and 0.25% of potassium persulfate, and polymerized and formed into columnar pellets of $2^{mm}\phi \times 2^{mm}$. The results are shown in the following table.

Additionally, the survival rate of live microorganisms is sought by the following equation.

The survival rate of live microorganisms $$(\%) = \frac{\text{Activity after immobilizing}}{\text{Activity before immobilizing}} \times 100$$

where the activity of live microorganisms is measured by the method of respiration rate.

|  | POLYETHLENE GLYCOL ACRYLATE | POLYMETHYLENE GLYCOL METHACRYLATE | ACRYLAMIDE |
|---|---|---|---|
| THIS INVENTION | 23% | 20% | 15% |
| CONVENTIONAL METHOD | 10% | 9% | 8% |

In consequence, according to the present invention, the substances toxic to the microorganisms of the polymerization initiator (hydroquinone or hydroquinone monomethyl ether) and the like are diffused in the solution of calcium chloride when calcium chloride is dropped, and become low in concentration, so that the survival rate of live microorganisms is remarkably high and the microorganisms show high activity.

Since polymerization is initiated simultaneously with dropping, the immobilizing material does not leak through a capsule of calcium alginate and gels satisfactorily.

Further, even the nitrification bacteria, whose cultures are difficult to be thickened, can be entrappingly immobilized by the method of the present invention. Namely, according to the present invention, the nitrification bacteria can be regulated to a high concentration, applied to the method of immobilizing the microorganisms according to the present invention, and improved.

Description will hereunder be given of a method of culturing and thickening of nitrification bacteria and of an example, wherein the thickened nitrification bacteria are immobilized in acrylamide monomer.

The method of immobilizing nitrification bacteria according to the present invention features that nitrification bacteria are previously adhered to a salt of alkali earth metal, the salt adhered thereto with the nitrification bacteria is separated by the natural sedimentation, and immobilized into hydrated gel of polyacrylamide.

As salts of alkali earth metals used in the present invention, there may be listed calcium phosphate, calcium chloride, magnesium phosphate, magnesium sulfate and the like, for example.

When nitrification bacteria are adhered to the surfaces of fine particles of alkali earth metal, the sedimenting properties of nitrification bacteria are improved, the concentration of the bacteria can be raised to a considerable extent with no complicated operation of separating solid from liquid. In consequence, the microorganisms of a high concentration can be immobilized in hydrated gel.

Alkali earth metal gives no harmful action to nitrification bacteria, and can control pH lowering due to nitrate ions generated by the action of nitrification bacteria.

Description will hereunder be given of an example, wherein nitrification bacteria is thickened to a high concentration and a method of immobilizing the thickened bacteria in acrylamide.

EXAMPLE 5

Calcium phosphate of 100 mg/l was added to a reaction tank, in which suspended type nitrification bacteria MLSS of 6000 mg/l is acclimatized, and further the culture was continued for about one month. As the result, nitrification bacteria adhered to the surfaces of calcium salt, and, when subjected to the natural sedimentation, MLSS, which would otherwise has been 10000 mg/l, was raised to 30000 mg/l.

The nitrification bacteria thus thickened was mixed with water solution containing 1.5% of sodium alginate, 18% of acrylamide monomer and 1% of N,N'-methylene-bis-acrylamide (crosslinker). Dimethylaminopropyonitrile of 0.5% as the polymerization promoter and peroxo potassium disulfate of 0.25% as the polymerization initiator were added to the mixed solution thus obtained, and polymerized at about 30 C. Polyacrylamide gel thus obtained is formed into columnar pellets each having a diameter of 3 mm and a height of 3 mm.

The columnar pellets thus obtained are filled in a fluidized bed type aeration tank (7 l) with the packing ratio 10%, and synthetic waste water containing an ammoniacal compound containing nitrogen is continuously passed through this aeration tank. The results are shown in the following table.

Further, for the comparison, the same experiments as described above were performed in the case where the suspended bacteria are immobilized according to the conventional method, and the results are shown in the following table as the conventional method.

|  | ACTIVITY (mgO$_2$/l · gel · h) | NH$_4$ - N LOAD (Kg/m$^3$ gel · d) |
|---|---|---|
| THIS INVENTION | 400~600 mg/l | 1.5~2.0 |

| | ACTIVITY (mgO$_2$/l · gel · h) | NH$_4$ - N LOAD (Kg/m$^3$ gel · d) |
|---|---|---|
| CONVENTIONAL METHOD | 100~200 mg/l | 0.5~1.0 |

As apparent from the above table, according to the present invention, the bacteria can be immobilized at a high concentration as compared with the conventional method, the activity and the load can be taken at high values. Further, the calcium compound immobilized in the gel can control pH lowering due to the generation of NO$_3$, the activity of the bacteria can be taken at a value higher than before, so that the stable treatment can be achieved.

According to the present invention, nitrification bacteria can be adhered to calcium salt to raise the concentration of the nitrification bacteria, so that the concentration of the bacteria in the gel can be raised. In consequence, when the nitrification bacteria immobilized by the method of the present invention, waste water can be treated efficiently and at high load.

Additionally, it should be natural that the nitrification bacteria of high concentration cultured in this embodiment can be used for prepolymer such as polyurethane prepolymer or polyethylene glycol acrylate as described above.

It should be understood, however, that there is no intention to limit the invention to the specific forms disclosed, but on the contrary, the invention is to cover all modifications, alternate constructions and equivalents falling, within the spirit and scope of the invention as expressed in the appended claims.

What is claimed is:

1. A method of immobilizing microorganisms comprising the steps:
    mixing an activated sludge containing a suspension of organisms, alginic acid or water soluble alginate, and an acrylamide monomer to form a mixed solution; and
    dropping said mixed solution into a water solution of a polyvalent metal ion and persulfate,
    wherein simultaneously when said mixed solution is dropped, said alginic acid or water soluble alginate in said mixed solution is combined with said polyvalent metal ion to become insoluble, whereby drops of said mixed solution are formed into particles in said water solution, and wherein in said particles the polymerization of said acrylamide monomer is initiated by said persulfate and said microorganisms are immobilized in said particles by entrapment.

2. A method of immobilizing microorganisms as set forth in claim 1, wherein a cross-linking agent together with said acrylamide monomer is added to said mixture.

3. A method of immobilizing microorganisms as set forth in claim 2, wherein said cross-linking agent is selected from the group consisting of N,N'-methylene-bis-acrylaimde, N,N'-propylene-bis-acrylamide, and diacrylamide dimethylester.

4. A method of immobilizing microorganisms as set forth in claim 1, wherein a polymerization promoter is added to said mixed solution prior to the dropping thereof and said polymerization promoter is β-dimethylaminopropinoitrile or N,N,N',N'-tetramethylethylenediamine.

5. A method of immobilizing microorganisms as set forth in claim 1, wherein said microorganisms contained in said activated sludge are nitrification bacteria, methane bacteria, Pseudomonous sp., or Flavobacterium sp.

6. A method of immobilizing microorganisms as set forth in claim 1, wherein said alginic acid or alginate in said mixed solution is present in an amount of from 0.3 to 1.2 wt%.

7. A method of immobilizing microorganisms as set forth in claim 1, wherein said polyvalent metal ion is calcium, barium, aluminum, or iron.

8. A method of immobilizing microorganisms comprising the steps of:
    mixing an activated sludge containing a suspension of microorganisms, alginic acid or water soluble alginate, and a prepolymer comprising an acrylic acid group and polyethylene glycol bonded together by means of esterification to form a mixed solution; and,
    dropping said mixed solution into a water solution of a polyvalent metal ion and persulfate,
    wherein, simultaneously when said mixed solution is dropped, said alginic acid or water soluble alginate in said mixed solution is combined with said polyvalent metal ion to become insoluble, whereby drops of said mixed solution are formed into particles in said water solution, and wherein in said particles the polymerization of said prepolymer is initiated by said persulfate and said microorganisms are immobilized in said particles by entrapment.

9. A method of immobilizing microorganisms as set forth in claim 8, wherein said acrylic acid group includes acrylic acid or methacrylic acid.

10. A method of immobilizing microorganisms as set forth in claim 8, wherein a polymerization promoter is added to said water solution prior to the dropping of said mixed solution and said polymerization promoter is selected from β-dimethylaminopropionitrile or N,N,N',N'-tetramethylenediamine.

11. A method of immobilizing microorganisms as set forth in claim 8, wherein said microorganisms are contained in said activated sludge are nitrification bacteria, methane bacteria, Pseudomonous sp., or Flavobacterim sp.

* * * * *